United States Patent
Kondo et al.

(10) Patent No.: US 10,561,400 B2
(45) Date of Patent: Feb. 18, 2020

(54) ULTRASONIC DIAGNOSTIC APPARATUS AND ULTRASONIC DIAGNOSTIC METHOD

(71) Applicant: CANON KABUSHIKI KAISHA, Tokyo (JP)

(72) Inventors: Kengo Kondo, Kyoto (JP); Makoto Yamakawa, Kyoto (JP); Tsuyoshi Shiina, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 654 days.

(21) Appl. No.: 14/780,488

(22) PCT Filed: Mar. 27, 2014

(86) PCT No.: PCT/JP2014/058837
§ 371 (c)(1),
(2) Date: Sep. 25, 2015

(87) PCT Pub. No.: WO2014/157510
PCT Pub. Date: Oct. 2, 2014

(65) Prior Publication Data
US 2016/0051231 A1 Feb. 25, 2016

(30) Foreign Application Priority Data
Mar. 28, 2013 (JP) .................. 2013-069852

(51) Int. Cl.
*A61B 8/00* (2006.01)
*A61B 8/08* (2006.01)
(Continued)

(52) U.S. Cl.
CPC ............... *A61B 8/485* (2013.01); *A61B 8/08* (2013.01); *A61B 8/5207* (2013.01); *A61B 8/54* (2013.01);
(Continued)

(58) Field of Classification Search
CPC .. A61B 8/485; A61B 8/08; A61B 8/54; A61B 8/5207; G01S 7/52022; G01S 15/8915; G01S 15/8959; G01S 7/52042
See application file for complete search history.

(56) References Cited

U.S. PATENT DOCUMENTS 6,155,980 A * 12/2000 Chiao ................. G01S 15/8959
600/447
2010/0286516 A1* 11/2010 Fan .......................... A61B 8/08
600/438
(Continued)

FOREIGN PATENT DOCUMENTS

CN 1218174 C 9/2005
CN 101869485 A 10/2010
(Continued)

OTHER PUBLICATIONS

Xiaojun Song, et al., A Base-Sequence Modulated Golay Code Improves the Excitation and Measurement of Ultrasonic Guided Waves in Long Bones, IEEE Transactions on Ultrasonics, Ferroelectrics, and Frequency Control, Nov. 2012, pp. 2580-2583, vol. 59, No. 11.

(Continued)

*Primary Examiner* — Joel Lamprecht
(74) *Attorney, Agent, or Firm* — Canon U.S.A., Inc. IP Division

(57) ABSTRACT

To provide an ultrasonic diagnostic apparatus and an ultrasonic diagnostic method capable of conducting ultrasonic diagnosis using acoustic radiation pressure, without causing an increase in the temperature of an ultrasound-exposed portion.
A push pulse transmitter outputs a coded pressurization pulse signal. A track pulse transmitter outputs a measurement pulse signal for measurement. An ultrasound probe outputs an ultrasonic wave for generating a shear wave in a (Continued)

target object on the basis of the pressurization pulse signal, and an ultrasonic wave for measurement on the basis of the measurement pulse signal. An echo receiver receives an echo of the ultrasonic wave for measurement, and outputs an electric signal. An elastic modulus estimator decodes the electric signal output by the echo receiver, and estimates an elastic modulus of the target object on the basis of the decoded signal.

16 Claims, 6 Drawing Sheets

(51) Int. Cl.
*G01S 7/52* (2006.01)
*G01S 15/89* (2006.01)

(52) U.S. Cl.
CPC ...... *G01S 7/52022* (2013.01); *G01S 7/52042* (2013.01); *G01S 15/8915* (2013.01); *G01S 15/8959* (2013.01)

(56) References Cited

U.S. PATENT DOCUMENTS

| 2012/0108968 A1 | 5/2012 | Freiburger et al. |
| 2012/0136250 A1 | 5/2012 | Tabaru |
| 2012/0158323 A1 | 6/2012 | Hazard |

FOREIGN PATENT DOCUMENTS

| CN | 102481143 A | 5/2012 |
| CN | 102641137 A | 8/2012 |
| CN | 102793556 A | 11/2012 |
| GB | 2428476 A | 1/2007 |
| JP | 2008-505669 A | 2/2008 |
| JP | 2012-024438 A | 2/2012 |
| JP | 2012-125549 A | 7/2012 |
| JP | 2012-170823 A | 9/2012 |
| WO | 2006/005632 A1 | 1/2006 |
| WO | 2011/126729 A | 10/2011 |

OTHER PUBLICATIONS

Todd N. Erpelding, et al., Bubble-Based Acoustic Radiation Force Using Chirp Insonation to Reduce Standing Wave Effects, Ultrasound in Med. & Biol., 2007, pp. 263-269, vol. 33, No. 2.

Martin P. Mienkina, et al., Experimental Evaluation of Photoacoustic Coded Excitation Using Unipolar Golay Codes, IEEE Transactions on Ultrasonics, Ferroelectrics, and Frequency Control, Jul. 2010, pp. 1583-1593, vol. 57, No. 7.

J. Bercoff et al.; "Supersonic Shear Imaging: A New Technique for Soft Tissue Elasticity Mapping," IEEE Trans. Ultrason., Ferroelectr., Freq. Control, pp. 396-409, vol. 51, No. 14, Apr. 2004.

Hideki Yoshikawa,et al.;"Effect of Burst Length and Amplitude of Push Pulse on Imaging Are in Ultrasonic Shear Wave Imaging"; Proceeding of Symposium on Ultrasonic Electronics; vol. 32; Nov. 8, 2011; pp. 275-276.

* cited by examiner

ULTRASONIC DIAGNOSTIC APPARATUS AND ULTRASONIC DIAGNOSTIC METHOD

TECHNICAL FIELD

The present invention relates to an ultrasonic diagnostic apparatus and an ultrasonic diagnostic method, and more particularly relates to an ultrasonic diagnostic apparatus and an ultrasonic diagnostic method using acoustic radiation pressure.

BACKGROUND ART

In diseases such as cancer, it is known that the condition of the disease is correlated with the hardness of the lesion. Knowing a hardness distribution within a living body contributes to very significant information in its diagnosis. One method of quantitatively obtaining the hardness of a tissue is a method that obtains an elasticity distribution from the velocity of shear wave propagation. In this method, a shear wave is generated within a living body, and the shear wave is measured using ultrasound, thereby estimating the propagation velocity.

As a method of generating a shear wave, a method of pressing a tissue in a living body using acoustic radiation pressure generated by emitting ultrasound has been recently proposed (for example, see NPL 1).

In the method described in NPL 1, an ultrasonic burst wave (push ultrasonic wave) of approximately hundreds of microseconds, for generating a shear wave, is emitted, and pressure (hereinafter may also be referred to as vibration) is applied using acoustic radiation. Thereafter, to observe the propagation of the shear wave generated within a target object, ultrasonic image measurements are performed at a recurrence frequency of about a few kHz (track ultrasonic wave). Observation using a track ultrasonic wave is generally performed for a duration of about a few ms to tens of ms. From the obtained image, a displacement distribution is measured, and the velocity of the shear wave propagation is estimated.

CITATION LIST

Non Patent Literature

NPL 1: J. Bercoff, M. Tanter, and M. Fink, "Supersonic Shear Imaging: A New Technique for Soft Tissue Elasticity Mapping," IEEE Trans. Ultrason., Ferroelectr., Freq. Control, pp. 396-409, Vol. 51, No. 14, APRIL 2004.

SUMMARY OF INVENTION

Technical Problem

However, this method requires the application of very strong energy within a short period of time, when compared with general diagnostic imaging. When such an ultrasonic wave is emitted, a failure such as an increase in the temperature of an ultrasound-exposed portion occurs, and thus improvement is necessary.

Therefore, an object of the present invention is to provide an ultrasonic diagnostic apparatus and an ultrasonic diagnostic method capable of conducting an ultrasonic diagnosis using acoustic radiation pressure, without causing an increase in the temperature of an ultrasound-exposed portion.

Solution to Problem

In order to solve the foregoing problem, an ultrasonic diagnostic apparatus according to the present invention includes a first pulse output unit that outputs a coded pressurization pulse signal;

a second pulse output unit that outputs a measurement pulse signal for measurement;

a probe that outputs an ultrasonic wave for generating a shear wave in a target object on the basis of the pressurization pulse, and an ultrasonic wave for measurement on the basis of the measurement pulse signal;

a receiver that receives an echo of the ultrasonic wave for measurement, and outputs an electric signal; and an elastic modulus estimator that decodes the electric signal output by the receiver, and estimates an elastic modulus of the target object on the basis of the decoded signal.

Since the pressurization pulse signal is a signal for pressurization, that is, since the pressurization pulse signal can only "push" and cannot "pull", the coded pressurization pulse signal uses unipolar codes. Preferably, the coded pressurization pulse signal is generated on the basis of a bipolar code. Preferably, the ultrasonic diagnostic apparatus further includes a displacement estimator. The displacement estimator estimates displacement by decoding the electric signal, output by the receiver, using the bipolar code, and the elastic modulus estimator estimates the elastic modulus on the basis of the estimated displacement.

Preferably, the first pulse output unit outputs the pressurization pulse signal in a case where a bit of the coded pressurization pulse signal is a first value, and does not output the pressurization pulse signal in a case where the bit of the coded pressurization pulse signal is a second value.

The coded pressurization pulse signal is preferably a pair of unipolar codes, and the pair of unipolar codes is generated by a bipolar code. The pair of unipolar codes includes a first unipolar code and a second unipolar code. A bit of the first unipolar code is "1" in a case where a bit of the bipolar code is "+1" and is "0" in a case where the bit of the bipolar code is "−1". A bit of the second unipolar code is "0" in a case where the bit of the bipolar code is "+1" and is "1" in a case where the bit of the bipolar code is "−1".

Preferably, the bipolar code is a Barker code.

Preferably, in a case where the number of bits of the bipolar code is N and a number at which the displacement is estimated is M, in a first period, the first pulse output unit outputs the pressurization pulse signal or signals, the number of which ranges from 0 to N inclusive, on the basis of the first unipolar code every certain cycle, and the second pulse output unit outputs the measurement pulse signal (N+M) times at timings different from the pressurization pulse signal every cycle. In a second period, the first pulse output unit outputs the pressurization pulse signal or signals, the number of which ranges from 0 to N inclusive, on the basis of the second unipolar code every cycle, and the second pulse output unit outputs the measurement pulse signal (N+M) times at timings different from the pressurization pulse signal every cycle.

Preferably, the first pulse output unit outputs the pressurization pulse signal between adjacent measurement pulse signals.

Preferably, the ultrasonic diagnostic apparatus includes a displacement estimator, and the displacement estimator includes a first calculator that calculates a first unipolar code displacement signal that represents coded unipolar displacement on the basis of an ultrasonic echo at an adjacent point of time in the first period, and calculates a second unipolar code displacement signal that represents coded unipolar displacement on the basis of an ultrasonic echo at an adjacent point of time in the second period, a second calculator that calculates a bipolar code displacement signal that represents coded bipolar displacement as a difference between the first unipolar code displacement signal and the second unipolar code displacement signal, and a third calculator that calculates a signal that represents displacement by performing decoding using correlation processing of the bipolar code displacement signal and the bipolar code.

An ultrasonic diagnostic apparatus controlling method according to the present invention includes a step of outputting a coded pressurization pulse signal; a step of outputting an ultrasonic wave for generating a shear wave in a target object on the basis of the pressurization pulse signal; a step of outputting a measurement pulse signal for measurement; a step of outputting an ultrasonic wave for measurement on the basis of the measurement pulse signal; a step of receiving an echo signal of the ultrasonic wave for measurement, and outputting an electric signal; and a step of decoding the electric signal, and estimating an elastic modulus on the basis of the decoded electric signal.

Preferably, the ultrasonic diagnostic apparatus controlling method further includes a step of estimating displacement of the target object, wherein the step of estimating displacement estimates the displacement by decoding the electric signal, and the step of estimating an elastic modulus includes estimating the elastic modulus on the basis of the estimated displacement. Preferably, the coded pressurization pulse signal includes being coded with a pair of unipolar codes. The pair of unipolar codes is generated on the basis of a bipolar code. The step of estimating displacement includes a step of estimating displacement by decoding the electric signal, output on the basis of the received ultrasonic echo, using the bipolar code.

Preferably, the pair of unipolar codes is generated by the bipolar code. The pair of unipolar codes includes a first unipolar code and a second unipolar code. In a case where the number of bits of the bipolar code is N and a number at which the displacement is estimated is M, the step of outputting a pressurization pulse signal includes a step of outputting, in a first period, the pressurization pulse signal or signals, the number of which ranges from 0 to N inclusive, on the basis of the first unipolar code every certain cycle, and includes a step of outputting, in a second period, the pressurization pulse signal or signals, the number of which ranges from 0 to N inclusive, on the basis of the second unipolar code every cycle. The step of outputting a measurement pulse signal includes a step of outputting, in the first period, the measurement pulse signal (N+M) times at timings different from the pressurization pulse signal every cycle, and a step of outputting, in the second period, the measurement pulse signal (N+M) times at timings different from the pressurization pulse signal every cycle.

Preferably, the step of outputting a pressurization pulse signal includes a step of outputting the pressurization pulse signal between adjacent measurement pulse signals.

Advantageous Effects of Invention

According to the ultrasonic diagnostic apparatus and the ultrasonic diagnostic method according to the present invention, an ultrasonic diagnosis using acoustic radiation pressure can be conducted without causing an increase in the temperature of an ultrasound-exposed portion.

DESCRIPTION OF EMBODIMENTS

Hereinafter, an embodiment of the present invention will be described using the drawings.

Figure 1:
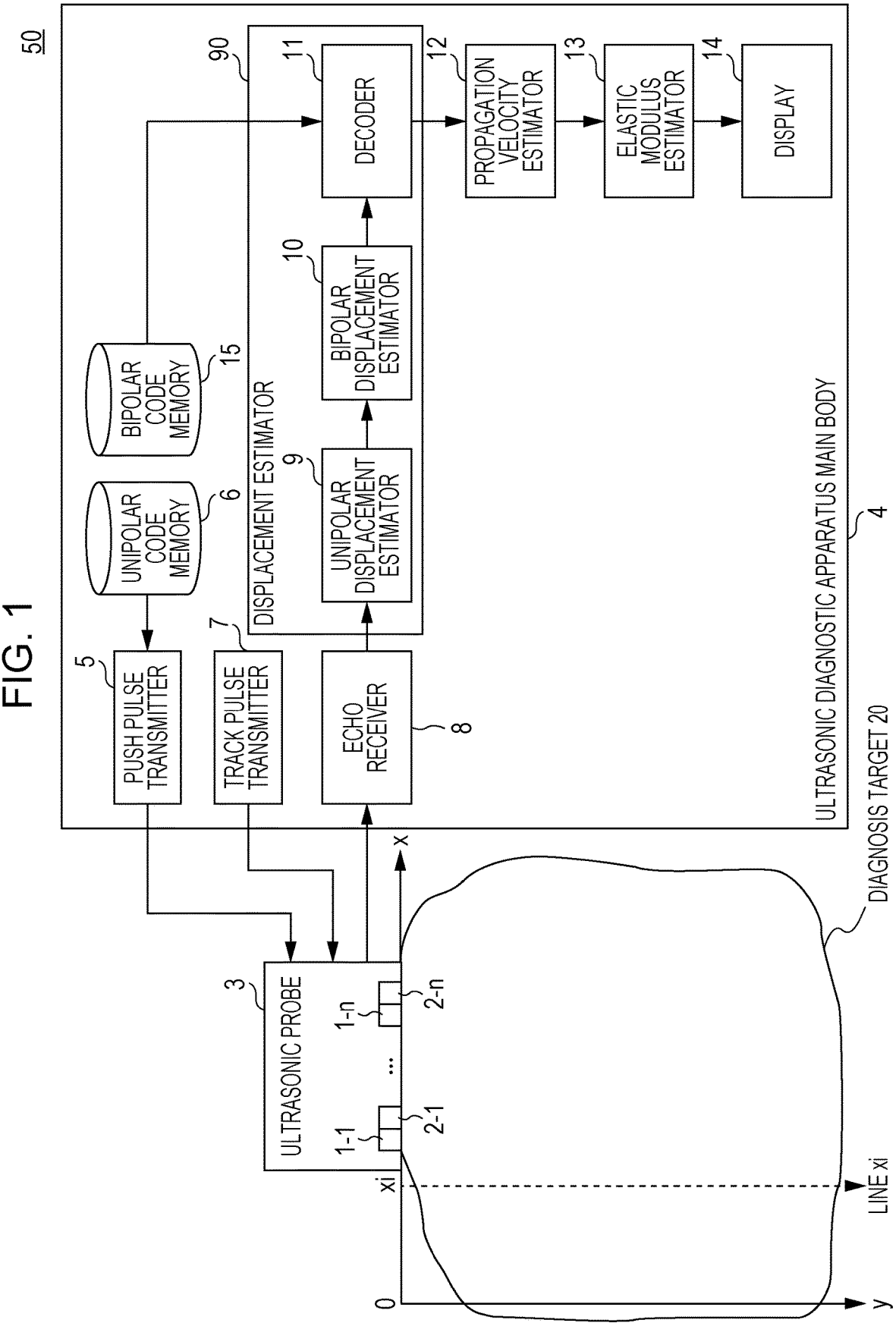
FIG. 1 is a diagram representing the configuration of an ultrasonic diagnostic apparatus according to an embodiment of the present invention.

FIG. 1 is a diagram representing the configuration of an ultrasonic diagnostic apparatus according to an embodiment of the present invention.

Referring to FIG. 1, an ultrasonic diagnostic apparatus 50 includes an ultrasound probe 3 and an ultrasonic diagnostic apparatus main body 4.

The ultrasound probe 3 includes transducers 1-1 to 1-n that are arranged in one dimension, and transducers 2-1 to 2-n that are arranged in one dimension.

The transducers 1-1 to 1-n output an ultrasonic plane wave that is ultrasound for measurement, and receive echoes (reflected waves of the ultrasound for measurement).

The transducers 2-1 to 2-n output an ultrasonic wave for generating a shear wave in a diagnosis target 20 that is a target object, thereby applying acoustic radiation pressure to the diagnosis target 20.

The ultrasonic diagnostic apparatus main body 4 includes a push pulse transmitter 5 that transmits a push pulse signal, which is a pressurization pulse signal, to the probe, a unipolar code memory 6, a track pulse transmitter 7 that transmits a track pulse signal, which is a measurement pulse signal, to the probe, an echo receiver (receiver) 8, a displacement estimator 90, a propagation velocity estimator 12, an elastic modulus estimator 13, a display 14, and a bipolar code memory 15. The displacement estimator 90 includes a unipolar displacement estimator 9, a bipolar displacement estimator 10, and a decoder 11.

The bipolar code memory 15 stores an N-bit Barker code $a[i]$ ($i=0$ to $N-1$). Here, $a[i]$ represents the i-th bit of the Barker code.

The unipolar code memory 6 stores a unipolar code $ap[i]$ ($i=0$ to $N-1$) representing a positive portion and $an[i]$ ($i=0$ to $N-1$) representing a negative portion, which constitutes one set generated on the basis of the Barker code $a[i]$. Using the N-bit Barker code $a[i]$, $ap[n]$ and $an[n]$ are represented by the following equations (1) and (2).

When $a[i]=+1, ap[i]=1$; and when $a[i]=-1, ap[i]=0$ (1)

When $a[i]=+1, an[i]=0$; and when $a[i]=-1, an[i]=1$ (2)

In the case of N=5, {a[i]}={+1, +1, +1, −1, +1}, {ap[i]}={1, 1, 1, 0, 1}, and {an[i]}={0, 0, 0, 1, 0}.

The push pulse transmitter 5 generates push pulses using the unipolar codes ap and an. The unipolar codes are used because application of pressure using acoustic radiation pressure can only "push" and cannot "pull". In a first period, the push pulse transmitter 5 transmits a first group of coded push pulses to the transducer 2-i at certain intervals in accordance with ap[0] to ap[N−1], thereby driving the transducer 2-i. In a second period, the push pulse transmitter 5 transmits a second group of coded push pulses to the transducer 2-i at certain intervals in accordance with an[0] to an[N−1], thereby driving the transducer 2-i.

In the first period and the second period, the track pulse transmitter 7 transmits track pulses at certain intervals to the transducer 1-i, thereby driving the transducer 1-i.

In the first period and the second period, the echo receiver 8 receives a signal based on an ultrasonic echo (reflected wave) output from the transducer 1-i, performs processing such as amplification, and outputs an electric signal (hereinafter may also be referred to as an echo electric signal).

The displacement estimator 90 includes the unipolar displacement estimator 9, the bipolar displacement estimator 10, and the decoder 11. The displacement estimator 90 estimates displacement from one earlier point of time by decoding the electric signal using a bipolar code.

From an electric signal in an adjacent point of time (frame), the unipolar displacement estimator 9 calculates a unipolar code displacement signal that represents coded unipolar displacement by using a displacement measurement method used in ultrasonic measurement.

From a unipolar code displacement signal in the first period and a unipolar code displacement signal in the second period, the bipolar displacement estimator 10 calculates a bipolar code displacement signal that represents coded bipolar displacement.

The decoder 11 calculates a bipolar displacement signal that represents displacement by performing decoding (pulse compression) using correlation processing of the Barker code a and the bipolar code displacement signal. Without performing coding such as that described in NPL 1, a signal equivalent to a signal obtained in the case where a large-amplitude push ultrasonic wave is applied for a very short period of time can be obtained.

On the basis of the bipolar displacement signal, the propagation velocity estimator 12 estimates the propagation velocity of the shear wave generated in the target object.

The elastic modulus estimator 13 calculates the elastic modulus (Young's modulus) on the basis of the velocity of shear wave propagation.

The display 14 displays a two-dimensional image having the elastic modulus as a pixel value.

(Operation)

Figure 2:
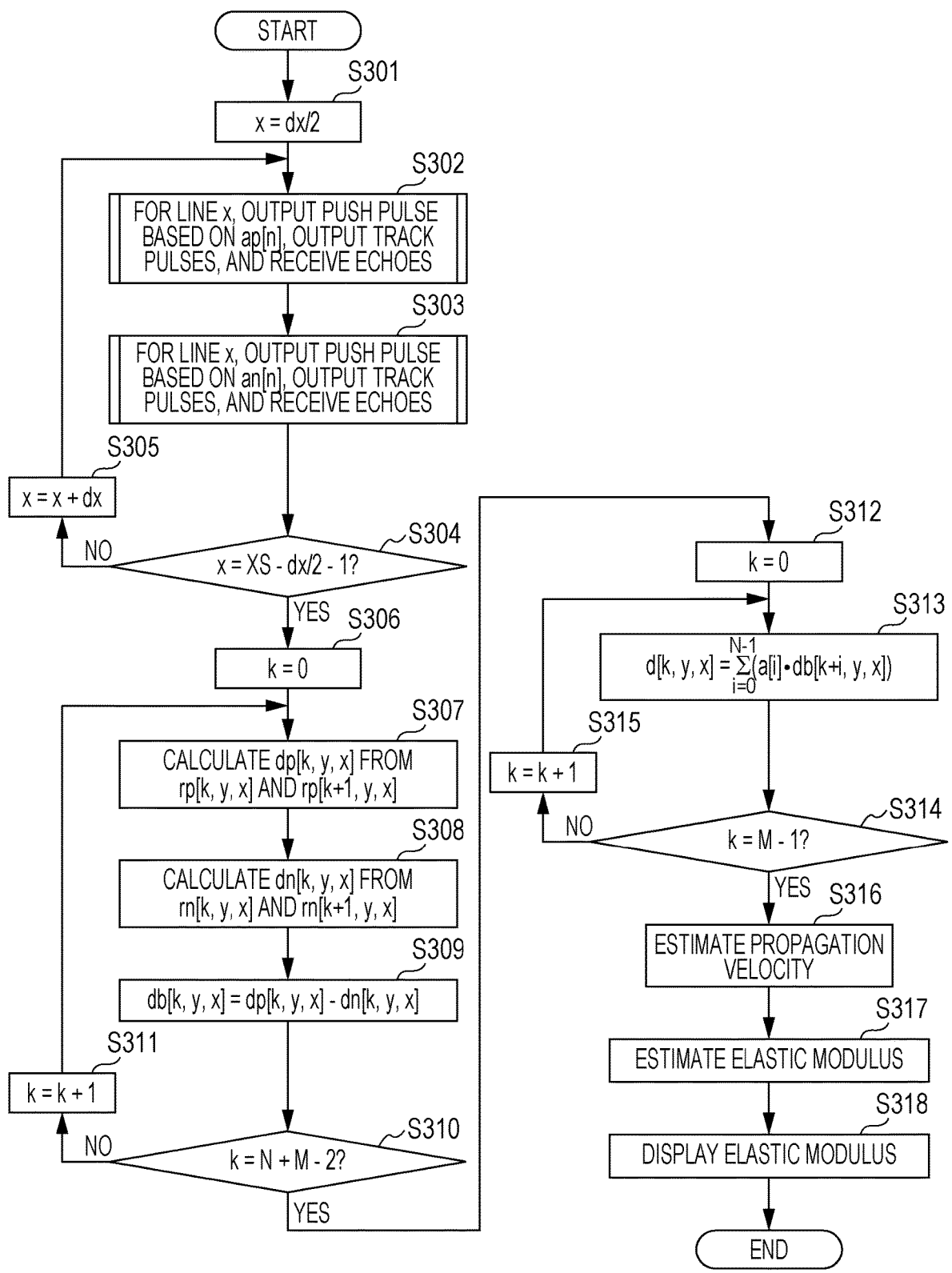
FIG. 2 is a flowchart representing the procedure of the operation of the ultrasonic diagnostic apparatus according to an embodiment of the present invention.

FIG. 2 is a flowchart representing the procedure of the operation of the ultrasonic diagnostic apparatus according to an embodiment of the present invention.

Referring to FIG. 2, in step S301, a variable x is set to "dx/2". The variable x represents the x coordinate of the diagnosis target 20, as illustrated in FIG. 1.

In step S302, the push pulse transmitter 5 outputs a push pulse signal based on the unipolar code ap[i] (i=0 to N−1). Upon receipt of the push pulse signal, the transducer 2-i positioned on the line x emits an ultrasonic wave (push ultrasonic wave) for generating a shear wave on the line x.

The track pulse transmitter 7 outputs (N+M) track pulse signals. Upon receipt of the track pulse signals, the transducers 1-1 to 1-n emit an ultrasonic plane wave for measurement. Here, N is the number of bits of the Barker code a and the unipolar codes ap and an. M is the number of frames of an image to be displayed on the display 14, that is, a number at a point of time at which displacement is estimated.

The transducers 1-1 to 1-n receive echoes of the ultrasonic wave for measurement (reflected waves). The echo receiver 8 generates electric signals rp[0, y, xα] to rp [N+M−1, y, xα] based on the ultrasonic echoes. Here, y is the y coordinate of the diagnosis target 20, which is calculated on the basis of a time t at which an ultrasonic echo is received, and the velocity of ultrasound. Also, y=0 to YS−1. YS is the size in the y direction (vertical direction) of a two-dimensional image to be displayed on the display 14. Here, xα=x−dx/2 to x+dx/2−1.

In step S303, the push pulse transmitter 5 outputs a push pulse signal based on the unipolar code an[i] (i=0 to N−1). Upon receipt of the push pulse signal, the transducer 2-i positioned on the line x emits an ultrasonic wave for generating a shear wave on the line x. The track pulse transmitter 7 outputs (N+M) track pulse signals. Upon receipt of the track pulse signals, the transducers 1-1 to 1-n emit an ultrasonic plane wave for measurement.

The transducers 1-1 to 1-n receive echoes of the ultrasonic wave for measurement. The echo receiver 8 generates electric signals rn[0, y, xα] to rn [N+M−1, y, xα] based on the ultrasonic echoes.

In step S304, in the case where the variable x is not equal to (XS−dx/2−1), the process proceeds to step S305; and, in the case where the variable x becomes equal to (XS−dx/2−1), the process proceeds to step S306. Note that XS is the size in the x direction (horizontal direction) of a two-dimensional image to be displayed on the display 14.

In step S305, the variable x is incremented only by "dx", and the process returns to step S302.

In step S306, a variable k is set to "0".

In step S307, the unipolar displacement estimator 9 calculates a unipolar code displacement signal dp[k, y, x] by using a displacement measurement method used in ultrasonic measurement, from an electric signal rp[k, y, x] based on an ultrasonic echo, and an electric signal rp[k+1, y, x] based on an ultrasonic echo.

Specifically, the unipolar displacement estimator 9 defines a window with a size W around a point for obtaining displacement, as indicated in equation (1), and obtains, as displacement, a point v at which a cross-correlation coefficient becomes maximum by performing template matching. Here, Δy is a distance representing a sampling interval in the y direction.

[Formula 1]

$$dp[k, y, x] = \Delta y \cdot \text{argmax}_v \left[ \frac{\sum_{w=-W/2}^{W/2} (rp[k, y+w, x] rp[k+1, y+v+w, x])}{\sqrt{\sum_{w=-W/2}^{W/2} (rp[k, y+w, x]^2) \sum_{w=-W/2}^{W/2} (rp[k+1, y+v+w, x]^2)}} \right] \quad (1)$$

In step S308, the unipolar displacement estimator 9 calculates a unipolar code displacement signal dn[k, y, x] by using a displacement measurement method used in ultrasonic measurement, from an electric signal rn[k, y, x] based on an ultrasonic echo, and an electric signal rn[k+1, y, x] based on an ultrasonic echo.

Specifically, the unipolar displacement estimator 9 defines a window with a size W around a point for obtaining displacement, as indicated in equation (2), and obtains, as displacement, a point v at which the cross-correlation coefficient becomes maximum by performing template matching. Here, Δy is a distance representing a sampling interval in the y direction.

[Formula 2]

$$dn[k, y, x] = \Delta y \cdot \mathrm{argmax}_v \left[ \frac{\sum_{w=-W/2}^{W/2}(rn[k, y+w, x]rn[k+1, y+v+w, x])}{\sqrt{\sum_{w=-W/2}^{W/2}(rn[k, y+w, x]^2)\sum_{w=-W/2}^{W/2}(rn[k+1, y+v+w, x]^2)}} \right] \quad (2)$$

In step S309, the bipolar displacement estimator 10 calculates a bipolar code displacement signal db[k, y, x] by subtracting the unipolar code displacement signal dn[k, y, x] from the unipolar code displacement signal dp[k, y, x].

In step S310, in the case where the variable k is not equal to (N+M−2), the process proceeds to step S311; and, in the case where the variable k becomes equal to (N+M−2), the process proceeds to step S312.

In step S311, the variable k is incremented only by "1", and the process returns to step S307.

In step S312, the variable k is set to "0".

In step S313, the decoder 11 calculates, for i=0 to N−1, the product of the i-th bit a[i] of the Barker code a and the bipolar code displacement signal db[k+i, y, x], and calculates the total sum of these products as a bipolar displacement signal d[k, y, x].

In step S314, in the case where the variable k is not equal to (M−1), the process proceeds to step S315; and, in the case where the variable k becomes equal to (M−1), the process proceeds to step S316.

In step S315, the variable k is incremented only by "1", and the process returns to step S313.

In step S316, the propagation velocity estimator 12 estimates a propagation time by using cross-correlation or the like on the basis of the bipolar displacement signal d[k, y, x], and then estimates the velocity cs[y, x] of shear wave propagation. Note that y=0 to YS−1, and x=0 to XS−1. Here, YS is the size in the y direction (vertical direction) of a two-dimensional image to be displayed on the display 14.

Specifically, the propagation velocity estimator 12 defines two points [y1, x1] and [y2, x2] in accordance with the direction of shear wave propagation, near a point [y, x] for obtaining elasticity, and estimates a propagation time τ[y, x] between the two points by using cross-correlation, as in the following equation. Here, Δt is an interval between a time point k and a time point k+1.

[Formula 3]

$$\tau[y, x] = \Delta t \cdot \mathrm{argmax}_v \left[ \frac{\sum_W (d[k+w, y_1, x_1]d[k+v+w, y_2, x_2])}{\sqrt{\sum_W (d[k+w, y_1, x_1]^2)\sum_W (d[k+v+w, y_2, x_2]^2)}} \right] \quad (3)$$

The propagation velocity estimator 12 obtains a shear wave propagation velocity cs[y, x] from the shear wave propagation time τ[y, x] by using the following equation. Here, l is a distance between the two points for which the propagation time has been obtained.

[Formula 4]

$$cs[y, x] = \frac{l}{\tau[y, x]} \quad (4)$$

In step S317, the elastic modulus estimator 13 obtains a rigidity modulus G[y, x] by using the following equation. Here, ρ is a density. Since a density distribution is generally unknown, an average density is used.

$$G[y,x]=\rho \times cs[y,x]^2 \quad (4)$$

The elastic modulus estimator 13 calculates a Young's modulus E[y, x] in accordance with the following equation. Here, ν is a Poisson's ratio, which can be regarded as substantially 0.5 in a soft biological tissue.

$$E[y,x]=2 \times G[y,x] \times (1+\nu) \quad (5)$$

In step S318, the display 14 displays a two-dimensional image in which a pixel value serves as E[y, x].

Figure 3:
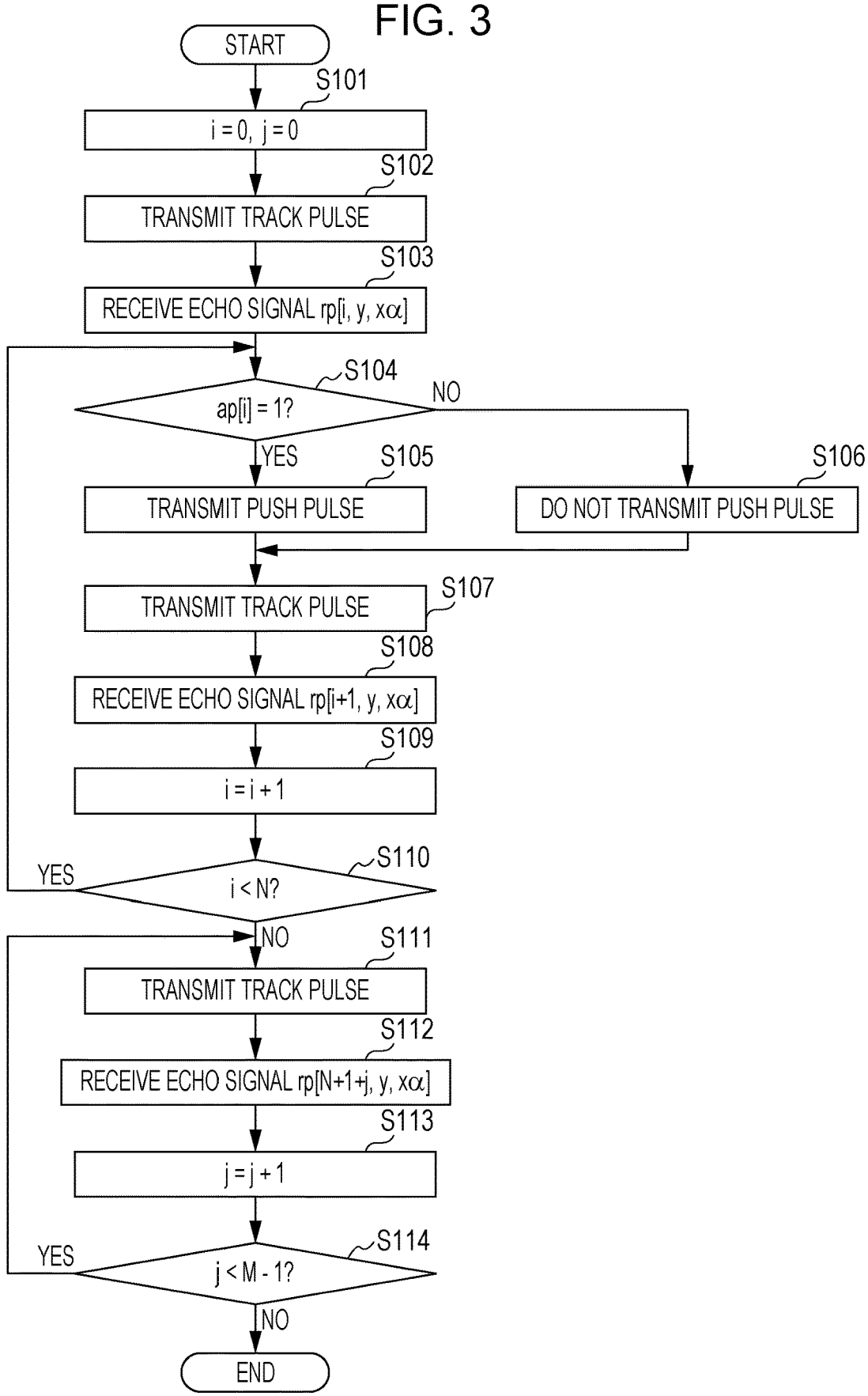
FIG. 3 is a flowchart representing the procedure of processing in step S302 in FIG. 2 in accordance with an embodiment of the present invention.

FIG. 3 is a flowchart representing the procedure of processing in step S302 in FIG. 2, in accordance with an embodiment of the present invention.

Referring to FIG. 3, in step S101, variables i and j are set to 0.

In step S102, the track pulse transmitter 7 transmits a track pulse signal. Upon receipt of the track pulse signal, the transducers 1-1 to 1-n emit a plane ultrasonic wave for measurement.

In step S103, the transducers 1-1 to 1-n receive echoes of the ultrasonic wave for measurement. The echo receiver 8 generates an electric signal rp[i, y, xα] based on the ultrasonic echoes by performing beam forming. As described above, y=0 to YS−1. Here, xα=x−dx/2 to x+dx/2−1.

In step S104, in the case where the unipolar code ap[i] is "1", the process proceeds to step S105; and, in the case where the unipolar code ap[i] is "0", the process proceeds to step S106.

In step S105, the push pulse transmitter 5 outputs a push pulse signal. Upon receipt of the push pulse signal, the transducer 2-i positioned on the line x emits an ultrasonic wave for generating a shear wave in a portion above the line x of the target object.

In step S106, the push pulse transmitter 5 does not output a push pulse signal, and the transducer 2-i positioned on the line x does not emit an ultrasonic wave for generating a shear wave in a portion above the line x of the target object.

In step S107, the track pulse transmitter 7 transmits a track pulse signal. Upon receipt of the track pulse signal, the transducers 1-1 to 1-n emit an ultrasonic plane wave for measurement.

In step S108, the transducers 1-1 to 1-n receive echoes of the ultrasonic wave for measurement. The echo receiver 8 generates an electric signal rp[i, y, xα] based on the ultrasonic echoes by performing beam forming. As described above, y=0 to YS−1. Here, xα=x−dx/2 to x+dx/2−1.

In step S109, the variable i is incremented only by "1".

In step S110, in the case where the variable i is less than the number N of frames, the process returns to step S104; and, in the case where the variable i becomes equal to the number N of frames, the process proceeds to step S111.

In step S111, the track pulse transmitter 7 transmits a track pulse signal. Upon receipt of the track pulse signal, the transducers 1-1 to 1-n emit a plane ultrasonic wave for measurement.

In step S112, the transducers 1-1 to 1-n receive echoes of the ultrasonic wave for measurement. The echo receiver 8 generates an electric signal rp[N+1+j, y, xα] based on the ultrasonic echoes by performing beam forming. As described above, y=0 to YS−1. Here, xα=x−dx/2 to x+dx/2−1.

In step S113, the variable j is incremented only by "1".

In step S114, in the case where the variable j is less than (M−1), the process returns to step S111; and, in the case where the variable j becomes equal to (M−1), the process ends.

As a result of the above operation, electric signals rp[0, y, xα] to rp [N+M−1, y, xα] based on the ultrasonic echoes are obtained. Since y=0 to YS−1 and xα=x−dx/2 to x+dx/2−1, YS×dx×(N+M) electric signals rp are obtained.

Figure 4:
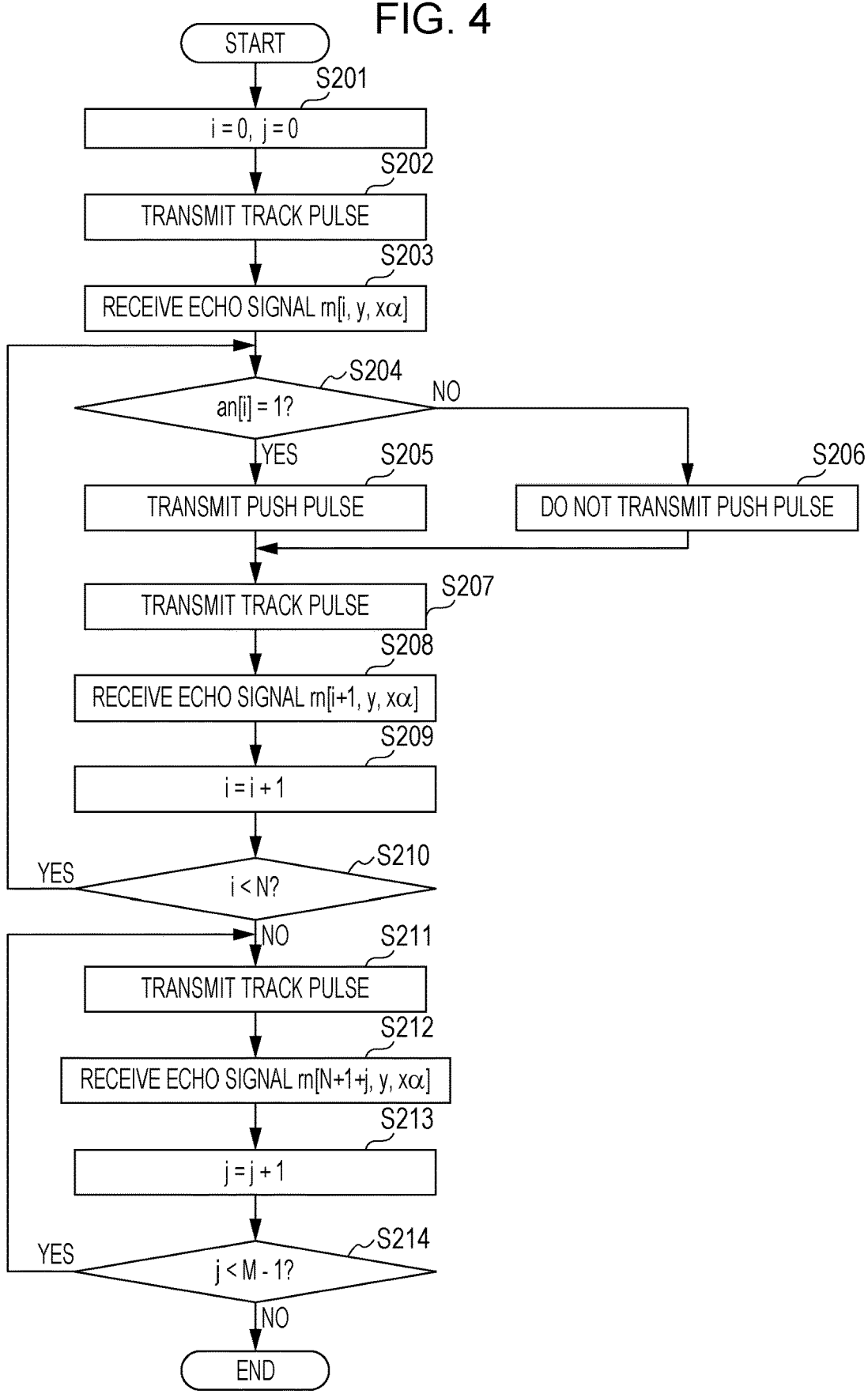
FIG. 4 is a flowchart representing the procedure of processing in step S303 in FIG. 2 in accordance with an embodiment of the present invention.

FIG. 4 is a flowchart representing the procedure of processing in step S303 in FIG. 2 in accordance with an embodiment of the present invention.

Referring to FIG. 4, in step S201, the variables i and j are set to 0.

In step S202, the track pulse transmitter 7 transmits a track pulse signal. Upon receipt of the track pulse signal, the transducers 1-1 to 1-n emit an ultrasonic plane wave for measurement.

In step S203, the transducers 1-1 to 1-n receive echoes of the ultrasonic wave for measurement. The echo receiver 8 generates an electric signal rn[i, y, xα] based on the ultrasonic echoes by performing beam forming. As described above, y=0 to YS−1. Here, xα=x−dx/2 to x+dx/2−1.

In step S204, in the case where the unipolar code an[i] is "1", the process proceeds to step S205; and, in the case where the unipolar code an[i] is "0", the process proceeds to step S206.

In step S205, the push pulse transmitter 5 outputs a push pulse signal. Upon receipt of the push pulse signal, the transducer 2-i positioned on the line x emits an ultrasonic wave for generating a shear wave in a portion above the line x of the diagnosis target 20.

In step S206, the push pulse transmitter 5 does not output a push pulse signal, and the transducer 2-i positioned on the line x does not emit an ultrasonic wave for generating a shear wave in a portion above the line x of the diagnosis target 20.

In step S207, the track pulse transmitter 7 transmits a track pulse signal. Upon receipt of the track pulse signal, the transducers 1-1 to 1-n emit an ultrasonic plane wave for measurement.

In step S208, the transducers 1-1 to 1-n receive echoes of the ultrasonic wave for measurement. The echo receiver 8 generates an electric signal rn[i, y, xα] based on the ultrasonic echoes by performing beam forming. As described above, y=0 to YS−1. Here, xα=x−dx/2 to x+dx/2−1.

In step S209, the variable i is incremented only by "1".

In step S210, in the case where the variable i is less than the number N of frames, the process returns to step S204; and, in the case where the variable i becomes equal to the number N of frames, the process proceeds to step S211.

In step S211, the track pulse transmitter 7 transmits a track pulse signal. Upon receipt of the track pulse signal, the transducers 1-1 to 1-n emit an ultrasonic plane wave for measurement.

In step S212, the transducers 1-1 to 1-n receive echoes of the ultrasonic wave for measurement. The echo receiver 8 generates an electric signal rn[N+1+j, y, xα] based on the ultrasonic echoes by performing beam forming. As described above, y=0 to YS−1. Here, xα=x−dx/2 to x+dx/2−1.

In step S213, the variable j is incremented only by "1".

In step S214, in the case where the variable j is less than (M−1), the process returns to step S211; and, in the case where the variable j becomes equal to (M−1), the process ends.

As a result of the above operation, electric signals rn[0, y, xα] to rn [N+M−1, y, xα] based on the ultrasonic echoes for measurement are obtained. Since y=0 to YS−1 and xα=x−dx/2 to x+dx/2−1, YS×dx×(N+M) electric signals rn are obtained.

(cf. a push pulse signal and a track pulse signal of related art (NPL 1)).

Figure 5:
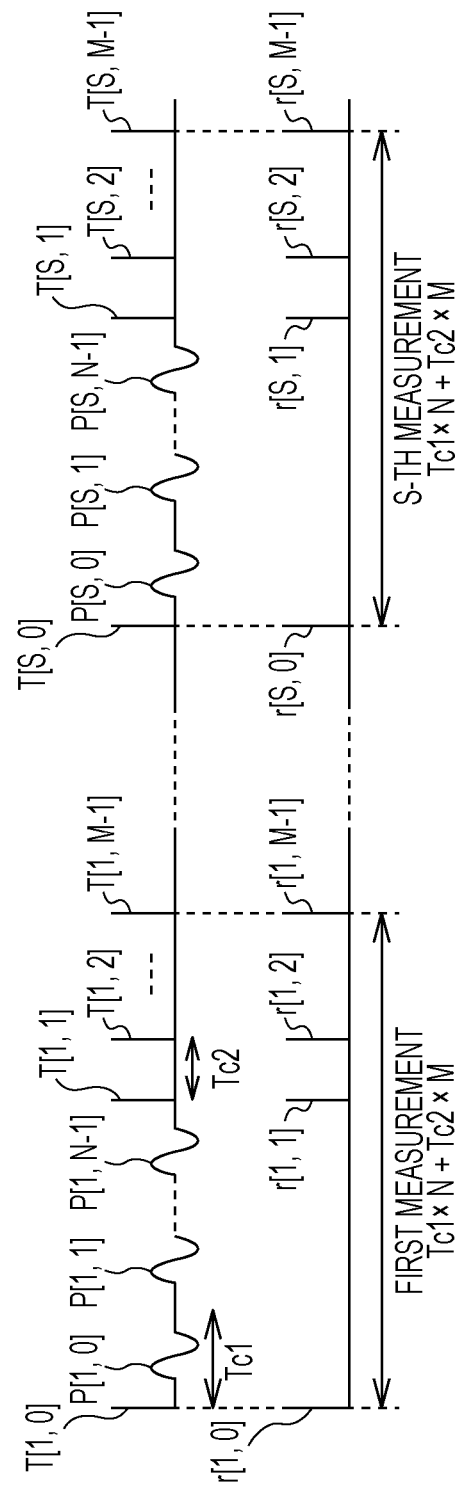
FIG. 5 is a diagram for describing measurements based on push pulses and track pulses of the related art.

FIG. 5 is a diagram for describing measurements based on a push pulse signal and a track pulse signal of the related art.

In the related art, measurements are repeated a plurality of times in order to obtain a certain precision, and the processing in steps S316 to S318 is performed using the ensemble average of electric signals based on the echoes of a measurement ultrasonic wave (track ultrasonic wave), which are the measurement results.

In the related art, a push pulse signal P[1, 0], P[1, 1], . . . , P[1, N−1] is output every cycle Tc1 in a first measurement, thereby emitting an ultrasonic wave for generating a shear wave in a target object. The push pulse signal is not coded, unlike ap and an in the embodiment, and is always output every cycle Tc1.

Before an ultrasonic wave for generating a shear wave in a target object is emitted on the basis of the push pulse signal, a track pulse signal T[1, 0] is output, thereby emitting an ultrasonic plane wave. In addition, after the ultrasonic wave for generating a shear wave in a target object is emitted on the basis of the push pulse signal, a track pulse signal T[1, 1], T[1, 2], . . . , T[1, M−1] is output every Tc2, thereby emitting an ultrasonic plane wave for measurement. Accordingly, electric signals r[1, 0], r[1, 1], . . . , r[1, M−1] based on echo signals of the ultrasonic wave for measurement are obtained.

In the related art, one measurement takes a time of Tc1×N+Tc2×M. If S measurements are done to obtain an ensemble average, a time of EN1=S×(Tc1×N+Tc2×M) is necessary in the related art.

(Push Pulse Signal and Track Pulse Signal According to Embodiment)

Figure 6:
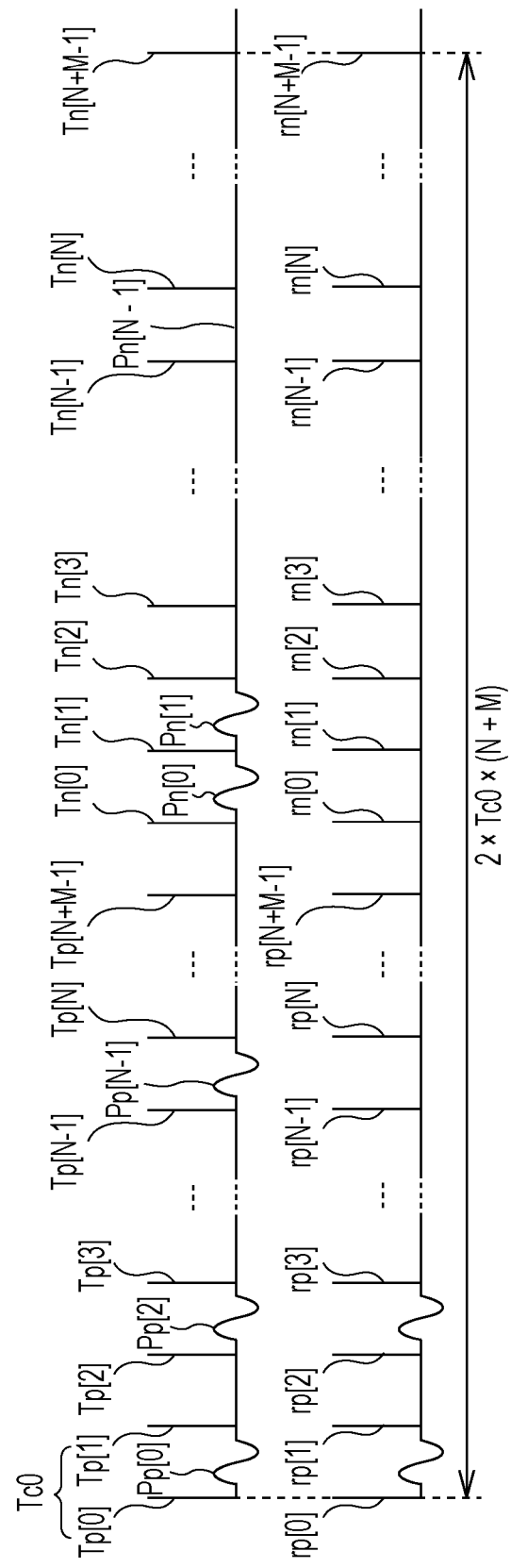
FIG. 6 is a diagram for describing measurements based on push pulses and track pulses according to the embodiment of the present invention.

FIG. 6 is a diagram for describing measurements based on a push pulse signal (pressurization pulse signal) and a track pulse signal (measurement pulse signal) according to an embodiment of the present invention.

In the embodiment, a track pulse signal Tp[0] to Tn[N+M−1] is output every cycle Tc0, thereby emitting an ultrasonic plane wave for measurement. In addition, at a timing between adjacent track pulse signals Tp, a push pulse signal (pressurization pulse signal) Pp[i] is output or not output on the basis of the unipolar code ap[i] (i=0 to N) every cycle Tc. Therefore, the number of push pulse signals Pp to be output is greater than or equal to 0 and less than or equal to N. In the case where the push pulse signal Pp[i] is output, an ultrasonic wave for generating a shear wave in a target object is emitted on the basis of that push pulse signal Pp[i].

Thereafter, a track pulse signal Tn[0] to Tn[N+M−1] is output every cycle Tc0, thereby emitting an ultrasonic plane wave for measurement. In addition, at a timing between adjacent track pulse signals Tn, a push pulse signal (pressurization pulse signal) Pn[i] is output or not output on the basis of the unipolar code an[i] (i=0 to N) every cycle Tc. Therefore, the number of push pulse signals Pn to be output is greater than or equal to 0 and less than or equal to N. In the case where the push pulse signal Pn[i] is output, an ultrasonic wave for generating a shear wave in a target object is emitted on the basis of that push pulse signal Pn[i].

The amplitude of a shear wave generated in a target object by an ultrasonic wave (push ultrasonic wave) transmitted in response to a push pulse signal according to the embodiment can be made significantly smaller than the amplitude of a shear wave generated by a push ultrasonic wave of the related art since the push pulse signal has been coded. In addition, Tc0 can be made longer than Tc1. Accordingly, in the embodiment, energy applied to the diagnosis target 20 per unit time can be made smaller than that in the related art, thereby preventing an increase in temperature.

In the embodiment, the measurement takes a time of EN2=2×Tc0×(N+M). In comparison of this time with the time EN1 (=S×(Tc1×N+Tc2×M)) of the related art, Tc0>Tc1 and Tc0>Tc2. According to an experiment conducted by the applicant of the present invention, it is indicated that the number S of times measurement is performed to obtain the ensemble average in the related art needs to be made considerably great in order to obtain measurement precision equivalent to the measurement precision of the embodiment. Therefore, the measurement time EN2 in the embodiment can be made, as a whole, smaller than the measurement time EN1 of the related art.

In the case of reducing incident energy simply by reducing the amplitude of acoustic radiation pressure or shortening the ultrasound exposure time, without using a coded pressurization pulse signal, the SNR (Signal to Noise Ratio) decreases in observation of the generated shear wave, thereby reducing the accuracy of estimating the propagation wave velocity. In contrast, SNR can be increased by obtaining an ensemble average by performing measurements a number of times. There is, however, the problem that the measurement time increases in proportion to the number of times measurement is performed to obtain the average. According to the present invention, in contrast to such technology (the technology of increasing SNR simply by reducing the amplitude of acoustic radiation pressure or shortening the ultrasound exposure time, without using a coded pulse signal, and by increasing the number of measurements), it becomes possible to conduct an ultrasonic diagnosis using acoustic radiation pressure in a short period of time, without causing an increase in temperature of an ultrasound-exposed portion.

Although the Barker code is used as an example of the bipolar code in the embodiment, the bipolar code is not limited thereto. Other binary codes such as the Golay code, the M-series code, and the Legendre symbol may be used.

In the case of the Golay code, specifically two Golay codes a[i] and b[i] (i=0 to N−1) are used.

The ultrasonic diagnostic apparatus uses {a[i]} to calculate a bipolar displacement signal d1[k, y, x] (k=0 to M−1, x=0 to XS−1, and y=0 to YS−1) by using a method that is the same as or similar to that described in the embodiment. Similarly, the ultrasonic diagnostic apparatus uses {b[i]} to calculate a bipolar displacement signal d2[k, y, x] (k=0 to M−1, x=0 to XS−1, and y=0 to YS−1) by using a method that is the same as or similar to that described in the embodiment. The ultrasonic diagnostic apparatus obtains the sum of the polar displacement signal d1[k, y, x] and the bipolar displacement signal d2[k, y, x] as a target bipolar displacement signal d[k, y, x].

Although displacement is calculated using template matching that uses cross-correlation as indicated in equations (1) and (2) in the embodiment, calculation of displacement is not limited thereto. For example, an IQ signal may be obtained by using quadrature detection from an echo signal, a phase difference of an RF signal may be estimated from an IQ signal between adjacent time points, and displacement may be calculated from the phase difference.

Although displacement from one earlier point of time is calculated in the embodiment, calculation of displacement is not limited thereto. Using displacement with reference to an initial value, decoding may be performed with a similar algorithm. Like displacement between adjacent frames, accumulated displacement from an initial value propagates through a shear wave. Therefore, elasticity estimation may be performed using displacement with reference to an initial value. Although the transmission cycle of a push pulse signal and the transmission cycle of a track pulse signal are described as the same cycle in the embodiment, the transmission cycles are not limited thereto. The transmission cycle of a track pulse signal may be shorter than the transmission cycle of a push pulse signal. In that case, displacement estimation can be performed with more track pulses, thereby further improving the measurement precision. Furthermore, it is more preferable that, in order to perform decoding with a high accuracy, the transmission cycle of a track pulse signal be one over an integer of the transmission cycle of a push pulse signal.

Although it is described in the embodiment that a track pulse signal is transmitted in the form of a plane wave, a track pulse signal is not limited to a plane wave. The transmission range of a track pulse signal may be limited within a range including an area for performing elasticity estimation. For example, the signal-to-noise ratio of a reflected signal can be increased by forming a transmission beam by performing so-called beam forming, and, by using a signal with a high signal-to-noise ratio obtained as a result thereof, the accuracy of estimating displacement is improved. When the accuracy of estimating displacement becomes higher, an apparatus capable of estimating elasticity with yet a higher accuracy can be provided.

Although the elastic modulus is estimated by performing displacement estimation and further calculating the propagation velocity in the embodiment, the elastic modulus can be directly estimated from a received signal without calculating displacement or propagation velocity itself if mathematically equivalent processing is performed.

Although it has been described in the embodiment that decoding is performed on a bipolar code displacement signal, a signal to be decoded is not limited thereto. For example, the advantageous effects of the present invention can also be achieved by decoding echo signals of an ultrasonic wave for measurement or a signal obtained by estimating displacement without performing decoding.

The embodiment disclosed here is exemplary in all points and is construed to be not restrictive. The scope of the present invention is indicated not by the above description but by the claims, and it is intended that all changes that have meanings equivalent to the scope of the claims and that are within the scope of the claims are included. For example, although the above description discusses the case in which displacement of a target object is estimated, the velocity of shear wave propagation is estimated on the basis of the estimated displacement, and then the elastic modulus is estimated, the configuration in which only displacement estimation or propagation velocity estimation is performed and elastic modulus estimation is not performed is also included in the scope of the present invention. Although an element for transmitting a push ultrasonic wave and an element for transmitting/receiving a track ultrasonic wave are separately provided in the probe 3, these operations may be performed with one element. In this case, there is an advantage that the probe can be made smaller. In addition, a probe for transmitting a push ultrasonic wave and a probe for transmitting/receiving a track ultrasonic wave may be separately provided. In this case, these probes can have a configuration (shape) appropriate for a push ultrasonic wave and a configuration (shape) appropriate for transmitting/receiving a track ultrasonic wave, resulting in design optimization.

The present application is based on and claims priority to Japanese Patent Application No. 2013-069852, filed on Mar. 28, 2013, in the Japan Patent Office, the entire disclosure of which is hereby incorporated by reference herein.

REFERENCE SIGNS LIST 1-1 to 1-n, 2-1 to 2-n transducers
3 ultrasound probe
4 ultrasonic diagnostic apparatus main body
5 push pulse transmitter
7 track pulse transmitter
8 echo receiver
9 unipolar displacement estimator
10 bipolar displacement estimator
11 decoder
12 propagation velocity estimator
13 elastic modulus estimator
14 display
50 ultrasonic diagnostic apparatus
90 displacement estimator

The invention claimed is:

1. An ultrasonic diagnostic apparatus comprising:
a first pulse output unit that outputs a coded pressurization pulse signal for causing a probe to generate a shear wave in a target object on the basis of the pressurization pulse signal;
a second pulse output unit that outputs a measurement pulse signal for causing the probe to generate an ultrasonic wave for measurement; and
an elastic modulus estimator that decodes the electric signal output by a receiver which has received an echo of the ultrasonic wave for measurement, and estimates an elastic modulus of the target object on the basis of the decoded signal;
wherein the first pulse output unit and the second pulse output unit outputs signals wherein one set of the coded pressurization pulse signals using N-bit code and the measurement pulse signals overlap each other in terms of time.

2. The ultrasonic diagnostic apparatus according to claim 1,
further comprising a displacement estimator that estimates displacement of the target object,
wherein the displacement estimator estimates displacement of the target object by decoding the electric signal output by the receiver, and the elastic modulus estimator estimates the elastic modulus of the target object on the basis of the estimated displacement.

3. The ultrasonic diagnostic apparatus according to claim 2,
wherein the coded pressurization pulse signal is coded with a pair of unipolar codes.

4. The ultrasonic diagnostic apparatus according to claim 3,
wherein the pair of unipolar codes is generated on the basis of a bipolar code, and the displacement estimator estimates displacement by decoding the electric signal using the bipolar code.

5. The ultrasonic diagnostic apparatus according to claim 4,
wherein the first pulse output unit outputs the pressurization pulse in a case where a bit of each of the unipolar codes is a first value, and does not output the pressurization pulse signal in a case where the bit of each of the unipolar code is a second value.

6. The ultrasonic diagnostic apparatus according to claim 5,
wherein the pair of unipolar codes is generated by the bipolar code, the pair of unipolar codes includes a first unipolar code and a second unipolar code, a bit of the first unipolar code is "1" in a case where a bit of the bipolar code is "+1" and is "0" in a case where the bit of the bipolar code is "−1", and a bit of the second unipolar code is "0" in a case where the bit of the bipolar code is "+1" and is "1" in a case where the bit of the bipolar code is "−1".

7. The ultrasonic diagnostic apparatus according to claim 6,
wherein the bipolar code is a Barker code.

8. The ultrasonic diagnostic apparatus according to claim 6,
wherein, in a case where the number of bits of the bipolar code is N and a number at which the displacement is estimated is M, in a first period, the first pulse output unit outputs the pressurization pulse signal or signals, the number of which ranges from 0 to N inclusive, on the basis of the first unipolar code every certain cycle, and the second pulse output unit outputs the measurement pulse signal (N+M) times at timings different from the pressurization pulse signal said every cycle, and in a second period, the first pulse output unit outputs the pressurization pulse signal or signals, the number of which ranges from 0 to N inclusive, on the basis of the second unipolar code said every cycle, and the second pulse output unit outputs the measurement pulse signal (N+M) times at timings different from the pressurization pulse signal said every cycle.

9. The ultrasonic diagnostic apparatus according to claim 8, wherein the displacement estimator includes
a first calculator that calculates a first unipolar code displacement signal that represents coded unipolar displacement on the basis of the electric signal at an adjacent point of time in the first period, and calculates a second unipolar code displacement signal that represents coded unipolar displacement on the basis of the electric signal at an adjacent point of time in the second period, a second calculator that calculates a bipolar code displacement signal that represents coded bipolar displacement as a difference between the first unipolar code displacement signal and the second unipolar code displacement signal, and a third calculator that calculates a signal that represents displacement by performing decoding using correlation processing of the bipolar code displacement signal and the bipolar code.

10. An ultrasonic diagnostic apparatus controlling method comprising:

a step of outputting a coded pressurization pulse signal;

a step of outputting an ultrasonic wave for generating a shear wave in a target object on the basis of the pressurization pulse;

a step of outputting a measurement pulse signal for measurement;

a step of outputting an ultrasonic wave for measurement on the basis of the measurement pulse signal;

a step of receiving an echo signal of the ultrasonic wave for measurement, and outputting an electric signal; and a step of decoding the electric signal, and estimating an elastic modulus of the target object on the basis of the decoded signal;

wherein one set of the coded pressurization pulse signal using N-bit code and the measurement pulse signals overlap each other in terms of time.

11. The ultrasonic diagnostic apparatus controlling method according to claim 10, further comprising a step of estimating displacement of the target object, wherein the step of estimating displacement estimates the displacement by decoding the electric signal, and the step of estimating an elastic modulus estimates the elastic modulus on the basis of the estimated displacement.

12. The ultrasonic diagnostic apparatus controlling method according to claim 11, wherein the coded pressurization pulse signal is coded with a pair of unipolar codes.

13. The ultrasonic diagnostic apparatus controlling method according to claim 10, wherein the pair of unipolar codes is generated on the basis of a bipolar code, and the step of estimating displacement includes a step of estimating displacement by decoding the electric signal using the bipolar code.

14. The ultrasonic diagnostic apparatus controlling method according to claim 13, wherein the pair of unipolar codes is generated by the bipolar code, the pair of unipolar codes includes a first unipolar code and a second unipolar code, in a case where the number of bits of the bipolar code is N and a number at which the displacement is estimated is M, the step of outputting a pressurization pulse signal includes a step of outputting, in a first period, the pressurization pulse signal or signals, the number of which ranges from 0 to N inclusive, on the basis of the first unipolar code every certain cycle, and includes a step of outputting, in a second period, the pressurization pulse signal or signals, the number of which ranges from 0 to N inclusive, on the basis of the second unipolar code said every cycle, and the step of outputting a measurement pulse signal includes a step of outputting, in the first period, the measurement pulse signal (N+M) times at timings different from the pressurization pulse signal said every cycle, and a step of outputting, in the second period, the measurement pulse signal (N+M) times at timings different from the pressurization pulse said every cycle.

15. An ultrasonic diagnostic apparatus comprising:

a first pulse output unit that outputs a coded pressurization pulse signal for causing a probe to generate a shear wave in a target object on the basis of the pressurization pulse signal;

a second pulse output unit that outputs a measurement pulse signal for causing the probe to generate an ultrasonic wave for measurement; and a displacement estimator that decodes the electric signal output by a receiver which has received an echo of the ultrasonic wave for measurement, and estimates displacement of the target object on the basis of the decoded signal.

16. An ultrasonic diagnostic apparatus comprising:

a first pulse output unit that outputs a coded pressurization pulse signal for causing a probe to generate a shear wave in a target object on the basis of the pressurization pulse signal;

a second pulse output unit that outputs a measurement pulse signal for causing the probe to generate an ultrasonic wave for measurement; and a velocity estimator that decodes the electric signal output by a receiver which has received an echo of the ultrasonic wave for measurement, and estimates a velocity of the shear wave generated in the target object on the basis of the decoded signal.

* * * * *